(12) United States Patent
Mertoglu et al.

(10) Patent No.: US 9,089,128 B2
(45) Date of Patent: Jul. 28, 2015

(54) USE OF A N-VINYLLACTAM / VINYLIMIDAZOL COPOLYMER AS DISPERSING AGENT

(75) Inventors: Murat Mertoglu, Ludwigshafen (DE); Matthias Bratz, Maxdorf (DE); Jürgen Jakob, Rödersheim-Gronau (DE); Winfried Mayer, Bubenheim (DE); Stefan Fischer, Freinsheim (DE); Son Nguyen Kim, Hemsbach (DE); Charles W. Finch, Garner, NC (US)

(73) Assignee: BASF SE, Ludwigshafen (DE)

( * ) Notice: Subject to any disclaimer, the term of this patent is extended or adjusted under 35 U.S.C. 154(b) by 66 days.

(21) Appl. No.: 13/813,728

(22) PCT Filed: Aug. 3, 2011

(86) PCT No.: PCT/EP2011/063365
§ 371 (c)(1),
(2), (4) Date: Feb. 1, 2013

(87) PCT Pub. No.: WO2012/017006
PCT Pub. Date: Feb. 9, 2012

(65) Prior Publication Data
US 2013/0130905 A1 May 23, 2013

Related U.S. Application Data

(60) Provisional application No. 61/371,178, filed on Aug. 6, 2010.

(30) Foreign Application Priority Data

Aug. 6, 2010 (EP) ...................................... 10172120

(51) Int. Cl.
| | | |
|---|---|---|
| *A01N 57/18* | (2006.01) | |
| *A01N 25/04* | (2006.01) | |
| *A01N 25/30* | (2006.01) | |
| *A01N 43/56* | (2006.01) | |
| *A01N 57/20* | (2006.01) | |

(52) U.S. Cl.
CPC .............. *A01N 25/04* (2013.01); *A01N 25/30* (2013.01); *A01N 43/56* (2013.01); *A01N 57/20* (2013.01)

(58) Field of Classification Search
None
See application file for complete search history.

(56) References Cited

U.S. PATENT DOCUMENTS

| 2008/0075689 A1 | 3/2008 | Pierobon et al. |
| 2010/0075850 A1* | 3/2010 | Dieckmann et al. .......... 504/100 |

FOREIGN PATENT DOCUMENTS

| EP | 0544158 | 6/1993 |
| WO | WO-2005/123014 | 12/2005 |
| WO | WO-2008/064987 | 6/2008 |

OTHER PUBLICATIONS

Zinc pyrithione page of the Chemical Book, Feb. 13, 2010 [downloaded from the internet on Apr. 1, 2014 from the website http://web.archive.org/web/20100213000054/http://www.chemicalbook.com/ProductChemicalPropertiesCB6456070_EN.htm].*
Glyphosate 54 label dated Mar. 26, 2007 [downloaded on Apr. 2, 2014 from the internet website http://www.alligare.com/assets/pdf/Glyphosate_54_LABEL.pdf].*
BASF Extreme label [downloaded on Apr. 2, 2014 from the internet website http://agproducts.basf.us/products/label-and-msds/extreme-herbicide-label.pdf].*
"European Search Report of EP10172120", dated Feb. 16, 2011, 2 pages.
"International Search Report of PCT/EP2011/063365",mailed on Jun. 3, 2012, 3 pages.

* cited by examiner

*Primary Examiner* — Sue Liu
*Assistant Examiner* — Thor Nielsen
(74) *Attorney, Agent, or Firm* — Servilla Whitney LLC

(57) ABSTRACT

The present invention relates to a use of a copolymer comprising N-vinyllactam, and vinylimidazol or a quaternized vinylimidazol in polymerized form as dispersing agent in an aqueous composition containing a water-insoluble pesticide. Further on, it relates to an aqueous composition which contains a copolymer comprising in polymerized form at least 20 mol % N-vinyllactam, and at least 1 mol % vinylimidazol or a quaternized vinylimidazol, a water-insoluble pesticide, and a dissolved salt. The invention also relates to a method for preparing the said composition by mixing water, the water-insoluble pesticide, the salt and the copolymer. Another subject is a method for controlling phytopathogenic fungi and/or undesired plant growth and/or undesired attack by insects or mites and/or for regulating the growth of plants, where said composition is allowed to act on the particular pests, their habitat or the plants to be protected from the particular pest, the soil and/or on undesired plants and/or the useful plants and/or their habitat.

12 Claims, No Drawings

USE OF A N-VINYLLACTAM / VINYLIMIDAZOL COPOLYMER AS DISPERSING AGENT

CROSS-REFERENCE TO RELATED APPLICATIONS

This application is the national stage entry of PCT/EP2011/063365, filed on Aug. 3, 2011, which claims priority to European Patent Application No. EP10172120.7, filed on Aug. 6, 2010, and U.S. Provisional Application No. 61/371,178, filed on Aug. 6, 2010, all of which are incorporated herein by reference in their entireties.

TECHNICAL FIELD

Aspects of the invention relate to copolymers comprising N-vinyllactam, and vinylimidazole or a quaternized vinylimidazole in polymerized form as dispersing agent in an aqueous composition containing a water-insoluble pesticide. vinylimidazolevinylimidazole

BACKGROUND

Besides the optimization of the active ingredient properties, the development of an effective agent is of particular importance with regard to the industrial production and application of active ingredients. By formulating the active ingredient(s) correctly, an optimal balance must be found between properties, some of which are in conflict with each other, such as the biological activity, the toxicology, potential environmental effects, and the costs. Moreover, the formulation is a decisive factor in determining the shelf life and the user friendliness of a composition.

Agrochemical compositions comprising copolymers of N-vinyllactams are known:

WO 2008/064987 discloses a formulation comprising a pesticide and a copolymer, which contains a) N-vinylamide, such as vinylpyrrolidone, and b) vinylpyrridine, vinylpyrrdidine derivatives or N-vinylimidazole. A use of said copolymer is disclosed for increasing the systemicity of pesticides in formulations.

WO 2006/018113 discloses the use of water-soluble copolymers from (b1) nonionic monoethylenically unsaturated monomers, such as N-vinylpyrrolidone, and (b2) cationic monoethylenically unsaturated monomers, such as N-Vinylimidazole, as thickening agent for aqueous dispersions, for example in agrochemicals.

SUMMARY

One aspect of the invention relates to a use of a copolymer comprising N-vinyllactam, and vinylimidazole or a quaternized vinylimidazole in polymerized form as dispersing agent in an aqueous composition containing a water-insoluble pesticide. Another aspect of the invention relates to an aqueous composition which contains a copolymer comprising in polymerized form at least 20 mol % N-vinyllactam, and at least 1 mol % vinylimidazole or a quaternized vinylimidazole, a water-insoluble pesticide, and a dissolved salt. A third aspect of the invention relates to a method for preparing the said composition by mixing water, the water-insoluble pesticide, the salt and the copolymer. Yet another aspect of the invention pertains to a method for controlling phytopathogenic fungi and/or undesired plant growth and/or undesired attack by insects or mites and/or for regulating the growth of plants, where said composition is allowed to act on the particular pests, their habitat or the plants to be protected from the particular pest, the soil and/or on undesired plants and/or the useful plants and/or their habitat. Combinations of preferred embodiments with other preferred embodiments are within the scope of the present invention.

DETAILED DESCRIPTION

One or more aspects of the present invention provide a polymer which allows dispersing a water-insoluble pesticide in aqueous compositions, especially in compositions comprising high concentrations of salts.

Accordingly, one aspect of the invention relates to the use of a copolymer comprising a) N-vinyllactam [comonomer a)], and b) vinylimidazolevinylimidazolee or a quaternized vinylimidazolevinylimidazolee [comonomer b)] in polymerized form as dispersing agent in an aqueous composition containing a water-insoluble pesticide. Preferably, the composition contains at least 5 wt % of a dissolved salt. The salt preferably contains an anionic pesticide.

The dispersing agent increases usually the storage stability of the aqueous composition. Preferably, the storage stability of the water-insoluble pesticide is increased, which may be present in emulsified and/or suspended form in the aqueous composition. Storage stability means that the degree of phase separation is visibly reduced upon storage (e.g. when stored at 20° C. for two weeks). Preferably, less coalescence, sedimentation or flocculation of the water-insoluble pesticide may be found upon storage.

The present invention also relates to an aqueous composition which contains a copolymer comprising in polymerized form
 a) at least 20 mol % N-vinyllactam, and
 b) at least 1 mol % vinylimidazolevinylimidazolee or a quaternized vinylimidazolevinylimidazolee;
a water-insoluble pesticide; and
a dissolved salt.

Comonomer a) is a N-vinyllactam. Suitable N-vinyllactams are N-vinyl lactams having 4 to 13 carbon atoms in the lactam ring. Examples are N-vinyl-2-pyrrolidone, N-vinylcaprolactam, N-vinylvalerolactam, N-vinyllaurolactam, N-vinyl-2-piperidone, N-vinyl-2-pyridone, N-vinyl-3-methyl-2-pyrrolidone, N-vinyl-4-methyl-2-pyrrolidone and/or N-vinyl-5-methyl-2-pyrrolidone. It is preferred to use N-vinyl-2-pyrrolidone, N-vinylcaprolactam and/or N-vinyl-2-piperidone. More preferred N-vinyl lactams are N-vinylpyrrolidone, N-vinylcaprolactam or mixtures thereof. Particularly preferred is N-vinylpyrrolidone ("VP").

Comonomer b) is a vinylimidazolevinylimidazolee or a quaternized vinylimidazolevinylimidazolee. Preferably, comonomer b) is vinylimidazolevinylimidazolee ("VI").

The imidazolyl moieties of vinylimidazolevinylimidazolee may be quaternized. The conversion of comonomers b) to quaternary compounds can take place during or, preferably, after the reaction. In the case of a subsequent conversion, the intermediate polymer can be isolated and purified first or converted directly. The conversion can be total or partial. Preferably at least 10%, particularly preferably at least 20% and very particularly preferably at least 30% of the incorporated comonomers (b) are converted to the corresponding quaternary form.

Preferably, the comonomers b) are used for the polymerization in predominantly cationogenic form, i.e. more than 70, preferably more than 90, particularly preferably more than 95 and very particularly preferably more than 99 mol % cationogenic, i.e. not in quaternized or protonated form, and only converted to the cationic or protonated form by quaternization during or, particularly preferably, after the polymerization.

In one preferred embodiment of the invention the resulting co-polymer is partially or completely protonated or quaternized only during or, particularly preferably, after the polymerization, because the comonomer b) used for the polymerization is preferably a comonomer that is only partially quaternized or protonated, if at all.

The comonomers b) can either be used in protonated or quaternized form or, preferably, polymerized in unquaternized or unprotonated form, the copolymer obtained in the latter case being either quaternized or protonated during or, preferably, after the polymerization for the use according to the invention.

In the case where the comonomers are used in quaternized form, they can be used either as the dried substance, or in the form of concentrated solutions in solvents suitable for the comonomers, e.g. in polar solvents such as water, methanol, ethanol or ace-tone, or in the other co-monomer a) provided these are suitable as solvents.

The resulting co-polymers may also be protonated. Examples of compounds suitable for the protonation are mineral acids such as HCl and $H_2SO_4$, monocarboxylic acids, e.g. formic acid and acetic acid, dicarboxylic acids and polyfunctional carboxylic acids, e.g. oxalic acid and citric acid, and any other proton-donating compounds and substances that are capable of protonating the appropriate nitrogen atom. Water-soluble acids are particularly suitable for the protonation.

Possible organic acids which may be mentioned are optionally substituted monobasic and polybasic aliphatic and aromatic carboxylic acids, optionally substituted monobasic and polybasic aliphatic and aromatic sulfonic acids or optionally substituted monobasic and polybasic aliphatic and aromatic phosphonic acids. Preferred organic acids are hydroxycarboxylic acids such as glycolic acid, lactic acid, tartaric acid and citric acid, lactic acid being particularly preferred. Preferred inorganic acids which may be mentioned are phosphoric acid, phosphorous acid, sulfuric acid, sulfurous acid and hydrochloric acid, phosphoric acid being particularly preferred.

The polymer may be protonated either directly after the polymerization or only when the respective pesticide is formulated, during which the pH is normally adjusted to a physiologically acceptable value. Protonation is understood as meaning that at least some of the protonatable groups of the polymer, preferably at least 20, preferably more than 50, particularly preferably more than 70 and very particularly preferably more than 90 mol %, are protonated, resulting in an overall cationic charge on the polymer.

Examples of suitable reagents for quaternizing the compounds a) are alkyl halides having 1 to 24 C atoms in the alkyl group, e.g. methyl chloride, methyl bromide, methyl iodide, ethyl chloride, ethyl bromide, propyl chloride, hexyl chloride, dodecyl chloride, lauryl chloride, propyl bromide, hexyl bromide, octyl bromide, decyl bromide, dodecyl bromide, and benzyl halides, especially benzyl chloride and benzyl bromide. Quaternization with long-chain alkyl radicals is preferably carried out with the corresponding alkyl bromides such as hexyl bromide, octylbromide, decylbromide, dodecyl bromide or lauryl bromide. Other suitable quaternizing agents are dialkyl sulfates, especially dimethyl sulfate or diethyl sulfate. The quaternization of the basic comonomers b) can also be carried out with alkylene oxides such as ethylene oxide or propylene oxide, in the presence of acids. Preferred quaternizing agents are methyl chloride, dimethyl sulfate or diethyl sulfate, methyl chloride being particularly preferred.

The quaternization of the comonomers or polymers with one of said quaternizing agents can be effected by generally known methods.

The copolymer may comprise optionally at least one additional comonomer c) in polymerized form. Suitable comonomers c) are nonionic ethylenically unsaturated monomers. Preferably, comonomer c) is an ethylenically unsaturated monomer, which is free of ionic or ionizable groups. Suitable comonomers c) are linear or branched $C_1$-$C_{20}$-alkyl (meth)acrylates, such as methyl acrylate, methyl methacrylate, ethyl acrylate, n-butyl acrylate, n-hexyl acrylate, n-octyl acrylate, n-decyl acrylate, 2-ethylhexyl acrylat, 2-propylheptyl acrylate, lauryl acrylate, stearyl acrylate, n-hexyl methacrylate, n-octyl methacrylate, n-decyl methacrylate, 2-ethylhexyl methacrylate, 2-propylheptyl methacrylate, lauryl methacrylate and stearyl methacrylate;

poly(ethylene glycol) (meth)acrylate or mono $C_{1-20}$ alkyl terminated poly(ethylene glycol) (meth)acrylate, for example those with one to 20 (preferably 3 to 15) ethylene glycol units. In a preferred form, the $C_{1-20}$ alkyl terminated poly(ethylene glycol) (meth)acrylate contains one to 50, preferably 3 to 40, and in particular 5 to 35 ethylene glycol units.

hydroxyalkyl (meth)acrylate, such as 2-hydroxyethyl acrylate, 2-hydroxypropyl acrylate, 3-hydroxypropyl acrylate, 2-hydroxyethyl methacrylate, 2-hydroxypropyl methacrylate and 3-hydroxypropyl methacrylate;

ethylenically unsaturated monomers containing an amide group, an N—$C_1$-$C_{18}$-alkylamide group or a N,N-di-$C_1$-$C_4$-alkylamide group, such as acrylamide, methacrylamide, N,N-dimethyl acrylamide or N,N-dimethyl methacrylamide;

vinylester of aliphatic $C_{1-32}$ carboxylic acids, such as vinyl acetate, vinyl propionate, vinyl laurate and vinyl stearate;

vinyl $C_1$-$C_4$-alkyl ether, such as vinyl methyl ether, vinyl ethyl ether;

vinyl aromatic monomers, such as styrene and vinyl toluene:

olefins with 2 to 20 carbon atoms, such as ethene, propene, 1-butene, isobutene, n-hexene, diisobutene, trimers and tetramers of butens or isobutens.

The copolymer may comprise up to 40 mol %, preferably up to 10 mol % and in particular up to 5 mol % of monomer c). In another preferred embodiment the copolymer may comprise up to 30 mol %, preferably up to 25 mol % of monomer c). In another preferred embodiment the copolymer consists of comonomers a) and b) in polymerized form.

The copolymer comprises usually a) at least 20 mol % N-vinyllactam, and b) at least 1 mol % vinylimidazolevinylimidazolee or a quaternized vinylimidazole in polymerized form. The copolymer comprises preferably a) at least 35 mol % N-vinyllactam, and b) at least 5 mol % vinylimidazole or a quaternized vinylimidazole in polymerized form. The copolymer comprises particularly preferably a) at least 40 mol % N-vinyllactam, and b) at least
10 mol % vinylimidazole or a quaternized vinylimidazole in polymerized form.

In another embodiment, the copolymer comprises usually a) up to 80 mol % N-vinyllactam, and b) up to 80 mol % vinylimidazole or a quaternized vinylimidazole in polymerized form. The copolymer comprises preferably a) up to 65 mol % N-vinyllactam, and b) up to 65 mol % vinylimidazole or a quaternized vinylimidazole in polymerized form.

In another embodiment, the copolymer comprises usually a) from 20 to 80 mol % N-vinyllactam, and b) from 20 to 80 mol % vinylimidazole or a quaternized vinylimidazole in polymerized form. The copolymer comprises preferably a) from 35 to 65 mol % N-vinyllactam, and b) from 35 to 65 mol % vinylimidazole or a quaternized vinylimidazole in polymerized form. In general, the mol % of comonomers a), b) and optional monomer c) add up to 100 mol %.

The molar ratio of comonomer a) to comonomer b) is usually in a range from 1:5 to 100:1, preferably from 1:2 to 50:1, in particular from 1:1.5 to 30:1, particularly preferably from 1:1.2 to 20:1, and very particularly preferably from 3:1 to 10:1.

The copolymer comprising a) N-vinyllactam, and b) vinylimidazole or a quaternized vinylimidazole in polymerized form and their preparation are known. Suitable processes may be found in WO 2008/064987 (example 2E), WO 94/10281 (examples polymer 8, 10, 11, 12) or DE 2814287 (example A5. and A6.).

Typically, the copolymer is a random copolymer or a block copolymer, wherein a random copolymer is preferred.

In a further embodiment, the copolymer is a graft copolymer. Typically, the graft co-polymer comprises a) N-vinyllactam, and b) vinylimidazole or a quaternized vinylimidazole, wherein both monomers a) and b) are grafted onto a polymer base. For example from 10 to 1000, preferably from 30 to 300 parts by weight of monomers a) and b) are grafted onto 100 parts by weight of the polymer base, such as polyalkylene glycols.

Suitable polymer bases are polyalkylene glycols and also the polyalkylene glycols blocked at one or both terminal groups with alkyl, carboxyl or amino groups (wherein alkyl is preferred). Preferred polyalkylene glycols are polyethylene glycol, polypropylene glycol and block copolymers of ethylene oxide and propylene oxide. The block copolymers may comprise ethylene oxide and propylene oxide in any desired amounts and incorporated in the form of polymerized units in any desired sequence. The terminal OH groups of the polyalkylene glycols can if appropriate be blocked with alkyl, carboxyl or amino groups at one or both ends, preferably with a $C_{1-20}$ alkyl group. It is preferable to use polyethylene glycol having a molecular weight MN in the range from 1000 to 100 000 as the grafting base and to graft it with vinyl acetate.

The composition contains usually from 0.1 to 40 wt % of the copolymer. Preferably, it contains from 1 to 20 wt % of the copolymer, in particular from 3 to 15 wt %, based on the total weight of the composition.

The aqueous composition comprises a water-insoluble pesticide. The water-insoluble pesticide can be selected from the group consisting of fungicides, insecticides, nematicides, herbicide and/or safener or growth regulator, preferably from the group consisting of fungicides, insecticides or herbicides. Suitable insecticides are insecticides from the class of the carbamates, organophosphates, organochlorine insecticides, phenylpyrazoles, pyrethroids, neonicotinoids, spinosins, avermectins, milbemycins, juvenile hormone analogs, alkyl halides, organotin compounds nereistoxin analogs, benzoylureas, diacylhydrazines, METI acarizides, and insecticides such as chloropicrin, pymetrozin, flonicamide, clofentezin, hexythiazox, etoxazole, diafenthiuron, propargite, tetradifon, chlorofenapyr, DNOC, buprofezine, cyromazine, amitraz, hydramethylnon, acequinocyl, fluacrypyrim, rotenone, or their derivatives. Suitable fungicides are fungicides from the classes of dinitroanilines, allylamines, anilinopyrimidines, antibiotics, aromatic hydrocarbons, benzenesulfonamides, benzimidazoles, benzisothiazoles, benzophenones, benzothiadiazoles, benzotriazines, benzyl carbamates, carbamates, carboxamides, carboxylic acid diamides, chloronitriles cyanoacetamide oximes, cyanoimidazoles, cyclopropanecarboxamides, dicarboximides, dihydrodioxazines, dinitrophenyl crotonates, dithiocarbamates, dithiolanes, ethylphosphonates, ethylaminothiazolecarboxamides, guanidines, hydroxy-(2-amino)pyrimidines, hydroxyanilides, imidazoles, imidazolinones, inorganic substances, isobenzofuranones, methoxyacrylates, methoxycarbamates, morpholines, N-phenylcarbamates, oxazolidinediones, oximinoacetates, oximinoacetamides, peptidylpyrimidine nucleosides, phenylacetamides, phenylamides, phenylpyrroles, phenylureas, phosphonates, phosphorothiolates, phthalamic acids, phthalimides, piperazines, piperidines, propionamides, pyridazinones, pyridines, pyridinylmethylbenzamides, pyrimidinamines, pyrimidines, pyrimidinonehydrazones, pyrroloquinolinones, quinazolinones, quinolines, quinones, sulfamides, sulfamoyltriazoles, thiazolecarboxamides, thiocarbamates, thiophanates, thiophenecarboxamides, toluamides, triphenyltin compounds, triazines, triazoles. Suitable herbicides are herbicides from the classes of the acetamides, amides, aryloxyphenoxypropionates, benzamides, benzofuran, benzoic acids, benzothiadiazinones, bipyridylium, carbamates, chloroacetamides, chlorocarboxylic acids, cyclohexanediones, dinitroanilines, dinitrophenol, diphenyl ether, glycines, imidazolinones, isoxazoles, isoxazolidinones, nitriles, N-phenylphthalimides, oxadiazoles, oxazolidinediones, oxyacetamides, phenoxycarboxylic acids, phenylcarbamates, phenylpyrazoles, phenylpyrazolines, phenylpyridazines, phosphinic acids, phosphoroamidates, phosphorodithioates, phthalamates, pyrazoles, pyridazinones, pyridines, pyridinecarboxylic acids, pyridinecarboxamides, pyrimidinediones, pyrimidinyl(thio)benzoates, quinolinecarboxylic acids, semicarbazones, sulfonylaminocarbonyltriazolinones, sulfonylureas, tetrazolinones, thiadiazoles, thiocarbamates, triazines, triazinones, triazoles, triazolinones, triazolocarboxamides, triazolopyrimidines, triketones, uracils, ureas.

The water-insoluble pesticide has usually a solubility in water of up to 10 g/l at 20° C. Preferably, the solubility in water is up to 1 g/l, in particular up to 0.5 g/l.

The aqueous composition may comprise from 0.01 to 50 wt % water-insoluble pesticide. Preferably, it comprises from 1 to 20 wt % water-insoluble pesticide.

The water-insoluble pesticide is preferably dispersed (e.g. emulsified and/or suspended) in the aqueous composition. The temperature, at which the water-insoluble pesticide is dispersed in the aqueous composition is usually at 20° C. In addition there might be water-insoluble pesticide present partly in dissolved form. Usually, at least 80 wt %, preferably at least 95 wt %, of the water-insoluble pesticide are dispersed (e.g. emulsified) in the aqueous composition. Preferably, the water-insoluble pesticide is emulsified in the aqueous composition.

Preferred water-insoluble pesticides are pyraclostrobin, difenoconazol, metconazole, fluxapyroxad, epoxiconazol, bixafen, preferably pyraclostrobin.

The aqueous composition may comprises at least one (e.g. one or two) dissolved salt. Preferably, it contains at least 5 wt % of the salt, more preferably at least 15 wt %, especially preferred at least 25 wt % and most especially preferred at least 35 wt %, based on the total weight of the aqueous composition. Mixtures of salts may also be present.

Suitable salts are all compounds which dissociate in water at 20° C. into at least one anion and at least one cation. Examples are inorganic salts and salts of organic compounds, whereas salts of organic compounds are preferred. More preferably, the salt contains an anionic pesticide.

The term "anionic pesticide" refers usually to at least one pesticide, which is present as an anion in the aqueous composition according to the invention. Usually, anionic pesticides comprise at least one anionic group. Preferably, the anionic pesticide comprises one or two anionic groups. In particular the anionic pesticide comprises exactly one anionic group. Suitable anionic groups are carboxylate, thiocarboxylate, sulfonate, sulfininate, thiosulfonate or phosphonate groups. A preferred example of an anionic group is a carboxylate group (—C(O)O—). The aforementioned anionic groups may be partly present in neutral form including a protonizable hydrogen. For example, the carboxylate group may be present partly in neutral form of carboxylic acid (—C(O)OH). This is preferably the case in aqueous compositions, in which an equilibrium of carboxylate and carboxylic acid may be present. Mixtures of anionic pesticides may be used.

Suitable anionic pesticides are given in the following. In case the names refer to a neutral form or a salt of the pesticide, the anionic form of the pesticides are meant.

Suitable anionic pesticides are herbicides, which comprise a carboxylate, thiocarboxylate, sulfonate, sulfininate, imidazolinone, thiosulfonate or phosphonate group, especially a carboxylate group. Examples are aromatic acid herbicides, phenoxycarboxylic acid herbicides, imidazolinone herbicides or organophosphorus herbicides comprising a carboxylic acid group.

Suitable aromatic acid herbicides are benzoic acid herbicides, such as chloramben, dicamba, 2,3,6-trichlorobenzoic acid (2,3,6-TBA), tricamba; pyrimidinyloxybenzoic acid herbicides, such as bispyribac, pyriminobac; pyrimidinylthiobenzoic acid herbicides, such as pyrithiobac; phthalic acid herbicides, such as chlorthal; picolinic acid herbicides, such as aminopyralid, clopyralid, picloram; quinolinecarboxylic acid herbicides, such as quinclorac, quinmerac; or other aromatic acid herbicides, such as aminocyclopyrachlor. Preferred are benzoic acid herbicides, especially dicamba.

Suitable imidazolinone herbicides are imazamethabenz, imazamox, imazapic, imazapyr, imazaquin and imazethapyr. Preferred are imazamox and imazapyr.

Suitable phenoxycarboxylic acid herbicides are phenoxyacetic herbicides, such as 4-chlorophenoxyacetic acid (4-CPA), (2,4-dichlorophenoxy)acetic acid (2,4-D), (3,4-dichlorophenoxy)acetic acid (3,4-DA), MCPA (4-(4-chloro-o-tolyloxy)butyric acid), MCPA-thioethyl, (2,4,5-trichlorophenoxy)acetic acid (2,4,5-T); phenoxybutyric herbicides, such as 4-CPB, 4-(2,4-dichlorophenoxy)butyric acid (2,4-DB), 4-(3,4-dichlorophenoxy)butyric acid (3,4-DB), 4-(4-chloro-o-tolyloxy)butyric acid (MCPB), 4-(2,4,5-trichlorophenoxy)butyric acid (2,4,5-TB); phenoxypropionic herbicides, such as cloprop, 2-(4-chlorophenoxy)propanoic acid (4-CPP), dichlorprop, dichlorprop-P, 4-(3,4-dichlorophenoxy)butyric acid (3,4-DP), fenoprop, mecoprop, mecoprop-P; aryloxy-phenoxypropionic herbicides, such as chlorazifop, clodinafop, clofop, cyhalofop, diclo-fop, fenoxaprop, fenoxaprop-P, fenthiaprop, fluazifop, fluazifop-P, haloxyfop, haloxyfop-P, isoxapyrifop, metamifop, propaquizafop, quizalofop, quizalofop-P, trifop. Preferred are phenoxyacetic herbicides, especially MCPA.

Suitable organophosphorus herbicides comprising a carboxylic acid group are bilanafos, glufosinate, glufosinate-P, glyphosate. Preferred is glyphosate.

Suitable other herbicides comprising a carboxylic acid are pyridine herbicides comprising a carboxylic acid, such as fluroxypyr, triclopyr; triazolopyrimidine herbicides comprising a carboxylic acid, such as cloransulam; pyrimidinylsulfonylurea herbicides comprising a carboxylic acid, such as bensulfuron, chlorimuron, foramsulfuron, halosulfuron, mesosulfuron, primisulfuron, sulfometuron.

Suitable anionic pesticides are fungicides, which comprise a carboxylate, thiocarboxylate, sulfonate, sulfininate, thiosulfonate or phosphonate group, especially a carboxylate group. Examples are polyoxin fungicides, such as polyoxorim.

Suitable anionic pesticides are insecticides, which comprise which comprise a carboxylate, thiocarboxylate, sulfonate, sulfininate, thiosulfonate or phosphonate group, especially a carboxylate group. Examples are thuringiensin.

Suitable anionic pesticides are plant growth regulator, which comprise a carboxylate, thiocarboxylate, sulfonate, sulfininate, thiosulfonate or phosphonate group, especially a carboxylate group. Examples are 1-naphthylacetic acid, (2-naphthyloxy)acetic acid, indol-3-ylacetic acid, 4-indol-3-ylbutyric acid, glyphosine, jasmonic acid, 2,3,5-triiodobenzoic acid, prohexadione, trinexapac, preferably prohexadione and trinexapac.

Preferred anionic pesticides are anionic herbicides, more preferably aromatic acid herbicides, phenoxycarboxylic acid herbicides or organophosphorus herbicides comprising a carboxylic acid group, particularly glyphosate.

The aqueous composition may comprise at least one anionic pesticide, such as one, two or three. Preferably, it comprises one.

The salt, such as the anionic pesticide, is preferably dissolved in the aqueous composition. The temperature, at which the salt is dissolved in the aqueous composition is usually at 20° C. In addition there might be anionic pesticide present partly in suspended or emulsified form. Usually, at least 80 wt %, preferably at least 95 wt %, of the anionic pesticide are dissolved in the aqueous composition.

The aqueous composition contains usually at least 10 wt % of the salt (e.g. the anionic pesticide), based on the total weight of the composition. Preferably, it contains at least 15 wt %, in particular at least 20 wt %, particularly preferably at least 30 wt % and very particularly preferably at least 35 wt %, based on the total weight of the composition. The composition may comprise up to 70 wt % of the salt (e.g. the anionic pesticide), preferably up to 60 wt %. For the calculation of the wt % of the anionic pesticide, the molecular weight of the anionic pesticide in the form of it anionic form (e.g. as carboxylate) without any cationic counterions is applied.

The aqueous composition may comprise—beside the water-insoluble pesticide and the anionic pesticide—further additional pesticides.

The aqueous composition usually comprises from 5 to 90 wt % water, preferably from 20 to 70 wt %, in particular from 35 to 65 wt %, based on the total weight of the composition.

The aqueous composition is may be in form of an emulsion, suspension or suspoemulsion. Preferably, the composition is an emulsion.

Typically, the water-insoluble pesticide is suspended, and/or emulsified in the aqueous composition. Preferably, water-insoluble pesticide is emulsified in the aqueous composition. When it is emulsified, the pesticide may form the emulsified phase by itself or in mixture with other compounds, such as an organic solvent. Preferably, the water-insoluble pesticide is emulsified in the aqueous composition, wherein the pesticide is dissolved in an organic solvent.

The aqueous composition may comprise an organic solvent. Usually, at least one water insoluble pesticide is dissolved in organic solvent. The organic solvent is preferably emulsified in the aqueous composition. In a preferred embodiment, the organic solvent has a solubility in the aqueous composition of up to 100 g/l at 20° C., preferably of up to 50 g/l, in particular of up to 5 g/l and particularly preferred of up to 1 g/l. In a further preferred embodiment, the organic solvent has a solubility in water of up to 150 g/l at 20° C., preferably of up to 100 g/l, in particular of up to 80 g/l and particularly preferred of up to 60 g/l.

The composition may comprise up to 40 wt %, preferably up to 30 wt % and in particular up to 20 wt % organic solvent, based on the total weight of the composition. In a further embodiment, the composition may comprise from 1 to 40 wt %, more preferably from 5 to 30 wt % organic solvent, based on the total weight of the composition.

Suitable organic solvents are for example mineral oil fractions of medium to high boiling point, such as solvent naphta (e.g. Solvesso® 200), kerosene or diesel oil; coal tar oils and oils of vegetable or animal origin; aliphatic, cyclic and aromatic hydrocarbons, e.g. toluene, xylene, paraffin, tetrahydronaphthalene; alkylated naphthalenes or their derivatives; alcohols such as methanol, ethanol, propanol, butanol, cyclohexanol, benzyl alcohol and o-sec-butyl phenol; glycols; ketones such as cyclohexanone; gamma-butyrolactone; fatty acid dimethylamides, such as N,N-dimethyldecanamide (e.g. Agnique® AMD 10), N,N-Dimethyloctanamide/decanamide (e.g. Agnique® AMD 810); fatty acids and fatty acid esters; amines such as N-methylpyrrolidone; ester, such as dibutyl adipate (Agnique® AE 6-4 Di), dimethyl adipate, 2-ethylhexyl lactate (e.g. Agnique® 3-2 EH, Purasolv® EHL); and mixtures of the aforementioned organic solvents. Preferred organic solvents are benzyl alcohol, o-sec-butyl phenol, solvent naphta, N,N-dimethyldecanamide, dibutyl adipate, dimethyl adipate, 2-ethylhexyl lactate, N,N-Dimethyloctanamide/decanamide. Most preferred solvents are benzyl alcohol, o-sec-butyl phenol, and solvent naphta. Mixtures of organic solvents may also be used.

The aqueous compositions according to the invention may also comprise auxiliaries which are customary in agrochemical compositions. The auxiliaries used depend on the particular application form and active substance, respectively. Examples for suitable auxiliaries are dispersants or emulsifiers (such as further solubilizers, protective colloids, surfactants and adhesion agents), organic and anorganic thickeners, bactericides, anti-freezing agents, anti-foaming agents, if appropriate colorants and tackifiers or binders (e. g. for seed treatment formulations).

Suitable surface-active substances (adjuvants, wetters, stickers, dispersants or emulsifiers) are the alkali metal, alkaline earth metal and ammonium salts of aromatic sulfonic acids, for example of lingo-(Borresperse® types, Borregaard, Norway), phenol-, naphthalene- (Morwet® types, Akzo Nobel, USA) and dibutylnaphthalenesulfonic acid (Nekal® types, BASF, Germany), and of fatty acids, alkyl- and alkylarylsulfonates, alkyl sulfates, lauryl ether sulfates and fatty alcohol sulfates, and salts of sulfated hexa-, hepta- and octadecanols and of fatty alcohol glycol ethers, condensates of sulfonated naphthalene and its derivatives with formaldehyde, condensates of naphthalene or of the naphthalenesulfonic acids with phenol and formaldehyde, polyoxyethylene octylphenol ether, ethoxylated isooctyl-, octyl- or nonylphenol, alkylphenyl polyglycol ethers, tributylphenyl polyglycol ethers, alkylaryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignin-sulfite waste liquors, and proteins, denatured proteins, polysaccharides (for example methylcellulose), hydrophobe-modified starches, polyvinyl alcohol (Mowiol® types, Clariant, Switzerland), polycarboxylates (Sokalan® types, BASF, Germany), polyalkoxylates, polyvinylamine (Lupamin® types, BASF, Germany), polyethyleneimine (Lupasol® types, BASF, Germany), polyvinylpyrrolidone, and their copolymers.

Surfactants which are particularly suitable are anionic, cationic, nonionic and amphoteric surfactants, block polymers and polyelectrolytes. Suitable anionic surfactants are alkali, alkaline earth or ammonium salts of sulfonates, sulfates, phosphates or carboxylates. Examples of sulfonates are alkylarylsulfonates, diphenylsulfonates, alpha-olefin sulfonates, sulfonates of fatty acids and oils, sulfonates of ethoxylated alkylphenols, sulfonates of condensed naphthalenes, sulfonates of dodecyl- and tridecylbenzenes, sulfonates of naphthalenes and alkylnaphthalenes, sulfosuccinates or sulfosuccinamates. Examples of sulfates are sulfates of fatty acids and oils, of ethoxylated alkylphenols, of alcohols, of ethoxylated alcohols, or of fatty acid esters. Examples of phosphates are phosphate esters. Examples of carboxylates are alkyl carboxylates and carboxylated alcohol or alkylphenol ethoxylates.

Suitable nonionic surfactants are alkoxylates, N-alkylated fatty acid amides, amine oxides, esters or sugar-based surfactants. Examples of alkoxylates are compounds such as alcohols, alkylphenols, amines (e.g. tallow amine), amides, arylphenols, fatty acids or fatty acid esters which have been alkoxylated. Ethylene oxide and/or propylene oxide may be employed for the alkoxylation, preferably ethylene oxide. Examples of N-alkylated fatty acid amides are fatty acid glucamides or fatty acid alkanolamides. Examples of esters are fatty acid esters, glycerol esters or monoglycerides. Examples of sugar-based surfactants are sorbitans, ethoxylated sorbitans, sucrose and glucose esters or alkylpolyglucosides. Examples of suitable cationic surfactants are quaternary surfactants, for example quaternary ammonium compounds with one or two hydrophobic groups, or salts of long-chain primary amines. Suitable amphoteric surfactants are alkylbetains and imidazolines. Suitable block polymers are block polymers of the A-B or A-B-A type comprising blocks of polyethylene oxide and polypropylene oxide or of the A-B-C type comprising alkanol, polyethylene oxide and polypropylene oxide. Suitable polyelectrolytes are polyacids or polybases. Examples of polyacids are alkali salts of polyacrylic acid. Examples of polybases are polyvinylamines or polyethyleneamines.

Examples for thickeners (i. e. compounds that impart a modified flowability to compositions, i. e. high viscosity under static conditions and low viscosity during agitation) are polysaccharides and organic and anorganic clays such as Xanthan gum (Kelzan®, CP Kelco, U.S.A.), Rhodopol® 23 (Rhodia, France), Veegum® (R.T. Vanderbilt, U.S.A.) or Attaclay® (Engelhard Corp., NJ, USA). Bactericides may be added for preservation and stabilization of the composition. Examples for suitable bactericides are those based on dichlorophene and benzylalcohol hemi formal (Proxel® from ICI or Acticide® RS from Thor Chemie and Kathon® MK from Rohm & Haas) and isothiazolinone derivatives such as alkylisothiazolinones and benzisothiazolinones (Acticide® MBS from Thor Chemie). Examples for suitable anti-freezing agents are ethylene glycol, propylene glycol, urea and glycerin. Examples for anti-foaming agents are silicone emulsions (such as e. g. Silikon® SRE, Wacker, Germany or Rhodorsil®, Rhodia, France), long chain alcohols, fatty acids, salts of fatty acids, fluoroorganic compounds and mixtures thereof. Examples for tackifiers or binders are polyvinylpyrrolidones, polyvinylacetates, polyvinyl alcohols and cellulose ethers (Tylose®, Shin-Etsu, Japan).

The present invention further relates to a method for preparing the aqueous composition according to the invention by mixing water, the water-insoluble pesticide and the copolymer. The method may be achieved at temperature from 5 to 100° C., preferably from 30 to 90° C., more preferably from 40 to 80° C.

In order to prepare an aqueous composition comprising an emulsified water-insoluble pesticide, the water-insoluble pesticide is preferably dissolved in the organic solvent and the solution is mixed with an aqueous composition which comprises the copolymer and optionally a salt, such as an anionic pesticide.

In order to prepare an aqueous composition comprising a suspended water-insoluble pesticide, the copolymer is mixed with the aqueous composition optionally comprising the salt (e.g. anionic pesticide), and then the water-insoluble pesticide is suspended therein (e.g. by bead milling).

In order to prepare an aqueous composition comprising a first emulsified water-insoluble pesticide and a second suspended water-insoluble pesticide, both aforementioned methods may be combined. The organic solvent used to prepare this suspoemulsion should be a bad solvent for the suspended pesticide, and a good solvent the emulsified pesticide that is dissolved in it.

The present invention further relates to a method for controlling phytopathogenic fungi and/or undesired plant growth and/or undesired attack by insects or mites and/or for regulating the growth of plants, where the aqueous composition according to the invention is allowed to act on the particular pests, their habitat or the plants to be protected from the particular pest, the soil and/or on undesired plants and/or the useful plants and/or their habitat.

Application can be carried out before or during sowing. Methods for applying or treating agrochemical compounds and compositions thereof, respectively, on to plant propagation material, especially seeds, are known in the art, and include dressing, coating, pelleting, dusting, soaking and in-furrow application methods of the propagation material. In a preferred embodiment, the compounds or the compositions thereof, respectively, are applied on to the plant propagation material by a method such that germination is not induced, e. g. by seed dressing, pelleting, coating and dusting. In a preferred embodiment, a suspension-type (FS) composition is used for seed treatment. Typically, a FS composition may comprise 1-800 g/l of active substance, 1-200 g/l Surfactant, 0 to 200 g/l antifreezing agent, 0 to 400 g/l of binder, 0 to 200 g/l of a pigment and up to 1 liter of a solvent, preferably water.

The active substances can be used as such or in the form of their compositions, e. g. in the form of directly sprayable solutions, suspensions, dispersions, emulsions, oil dispersions, by means of spraying, atomizing, dusting, spreading, brushing, immersing or pouring. The application forms depend entirely on the intended purposes; it is intended to ensure in each case the finest possible distribution of the pesticides. The active substance concentrations in the ready-to-use preparations can be varied within relatively wide ranges. In general, they are from 0.0001 to 10%, preferably from 0.001 to 1% by weight of active substance. The active substances may also be used successfully in the ultra-low-volume process (ULV), it being possible to apply compositions comprising over 95% by weight of active substance, or even to apply the active substance without additives.

When employed in plant protection, the amounts of active substances (also called pesticide) applied are, depending on the kind of effect desired, from 0.001 to 2 kg per ha, preferably from 0.005 to 2 kg per ha, more preferably from 0.05 to 0.9 kg per ha, in particular from 0.1 to 0.75 kg per ha. In treatment of plant propagation materials such as seeds, e. g. by dusting, coating or drenching seed, amounts of active substance of from 0.1 to 1000 g, preferably from 1 to 1000 g, more preferably from 1 to 100 g and most preferably from 5 to 100 g, per 100 kilogram of plant propagation material (preferably seed) are generally required. When used in the protection of materials or stored products, the amount of active substance applied depends on the kind of application area and on the desired effect. Amounts customarily applied in the protection of materials are, e. g., 0.001 g to 2 kg, preferably 0.005 g to 1 kg, of active substance per cubic meter of treated material.

Various types of oils, wetters, adjuvants, herbicides, bactericides, other fungicides and/or pesticides may be added to the active substances or the compositions comprising them, if appropriate not until immediately prior to use (tank mix). These agents can be admixed with the compositions according to the invention in a weight ratio of 1:100 to 100:1, preferably 1:10 to 10:1. Adjuvants which can be used are in particular organic modified polysiloxanes such as Break Thru S 240®; alcohol alkoxylates such as Atplus 245®, Atplus MBA 1303®, Plurafac LF 300® and Lutensol ON 30®; EO/PO block polymers, e. g. Pluronic RPE 2035® and Genapol B®; alcohol ethoxylates such as Lutensol XP 80®; and dioctyl sulfosuccinate sodium such as Leophen RA®.

The present invention has various advantages: The copolymer has excellent capabilities for dispersing (e.g. emulsifying) water-insoluble pesticides in aqueous compositions, especially when the composition has a high concentration of salts, such as anionic pesticides. The invention enables the preparation of stable fluid pesticides concentrates, especially with high concentrations of anionic pesticides, which could not be prepared with conventional dispersing agent. It is also now possible to combine a high concentration of an anionic pesticide and a water-insoluble pesticide in one aqueous formulation. This combination of pesticides makes the handling easier for farmers: they have to use a single agrochemical formulation instead of several separate ones, and they have to meter only a single formulation instead of two or more separate formulations, and finally this provides additional logistic advantages. Earlier combinations of a high concentration of an anionic pesticide and a water-insoluble pesticide in one formulation were only achieved in dry, dusty agrochemical formulation, which can now be avoided by non-dusty aqueous formulations.

EXAMPLES

VP/VI Copolymer: Granules of poly(vinylpyrrolidone-vinylimidazole), molar ratio VP:VI 1:1, average molar mass 68.000 to 73.000 g/mol (determined by GPC).

Dispersant A: ammonium salt of polyaryvinylethersulfat, viscous liquid, commercially available as Soprophor® 4 D 384 from Rhodia.

Surfactant: C8 alkyl glycoside, 65 wt % in water, viscosity 160 mPas at 30° C., commercially available as AG-6202 from Akzo Nobel.

Dispersant B: Comb polymer comprising in methyl methacrylate, methacrylic acid and methoxypolyethylene glycol methacrylate, 33 wt % in a 1:1 water: propylene glycol mixture, commercially available as Atlox® 4913 from Uniquema.

Dispersant C: Sodium salt of naphthalene sulfonate condensate, commercially as Morwet® D-425 powder from Akzo Nobel.

LUMA: acrylic acid ester of linear C16/18 fatty alcohol terminated poly(ethylene glycol) with about 25 mol ethylene glycol units per molecule.

QVI: quaternized viniyimidazol (quaternized with gaseous methyl chloride)
SMA: stearyl methacrylate

Example 1

Preparation of an Aqueous Emulsion (EW)

A pesticide mixture of 716.9 g aqueous glyphosate isopropylamine salt solution (68 wt % glyphosate free acid, corresponding to 487.5 g glyphosate free acid) and pyraclostrobin (37.5 g) was mixed in a beaker with 50 g Dispersant A, 50 g VP/VI Copolymer, 30 g Surfactant and 42.3 g benzylalcohol. The mixture was filled up to a final volume of 1.0 l and stirred for 30 minutes at 50° C. by using a dissolver disk, until pyraclostrobin dissolved in the benzyl alcohol emulsion droplets.

Example 2 to 4 and Comparative Examples C1 to C3

These examples were made as in example 1. Their composition is summarized in Table 1. Benzylalcohol and o-sec-butylphenol were used as organic solvents, and were insoluble in the aqueous composition due to the high salt concentration.

TABLE 1

Composition of agrochemical formulations (all compositions were prepared according to example 1 and filled up with water to a final volume of 1,0 l)

|  | 1 | 2 | 3 | 4 | C1 [a] | C2 [a] | C3 [a] |
|---|---|---|---|---|---|---|---|
| Glyphosate [b] | 487.5 | 487.5 | 487.5 | 487.5 | 487.5 | 487.5 | 487.5 |
| Pyraclostrobin | 37.5 | 37.5 | 37.5 | 37.5 | 37.5 | 37.5 | 37.5 |
| VP/VI Co-polymer | 50 | 80 | 50 | 50 | — | — | — |
| Dispersant A | 50 | 50 | 50 | 50 | 50 | 50 | 50 |
| Dispersant B | — | — | — | — | — | 50 | — |
| Dispersant C | — | — | — | — | — | — | 50 |
| Surfactant | 30 | 30 | 30 | 30 | 30 | 30 | 30 |
| Benzylalcohol | 42.3 | 42.3 | 42.3 | — | 42.3 | 42.3 | 42.3 |
| o-sec-Butylphenol | — | — | — | 42.3 | — | — | — |

[a] Comparative example, not according to the invention.
[b] Amount relates to glyphosate free acid.

Example 5

Storage stability

The formulations of example 1 to 4 and the comparative examples were stored at 20° C. or at 40° C. without moving them. Afterwards, they were visually inspected for phase separation of benzylalcohol emulsion droplets, which could coalescence and separate as for example in Entry C1 to C3 of Table 2. Table 2 summarizes the results, wherein "no" means that no phase separation was observed, whereas "yes" means that a phase separation was clearly visible. As a result, the storage stability was clearly increase when using poly(vinylpyrrolidone-vinylimidazole) as dispersing agent.

TABLE 2

Phase separation during storage

| Example | 1 h at 20° C. | 24 h at 20° C. | 14 d at 40° C. | 28 d at 20° C. |
|---|---|---|---|---|
| 1 | no | no | no | no |
| 2 | no | no | no | no |
| 3 | no | no | no | no |
| 4 | no | no | no | no |

TABLE 2-continued

Phase separation during storage

| Example | 1 h at 20° C. | 24 h at 20° C. | 14 d at 40° C. | 28 d at 20° C. |
|---|---|---|---|---|
| C1 [a] | yes | yes | yes | yes |
| C2 [a] | no | yes | yes | yes |
| C3 [a] | no | yes | yes | yes |

[a] Comparative example, not according to the invention.

Example 6

Composition of Polymers

The following copolymers were prepared with a composition of comonomers as described in Table 3 by precipitation polymerisation or polymerisation in solution according to known methods (e.g. described in WO 2007/010034, DE 10 2005 046 916, or EP 0 913 143).

TABLE 3

Composition of polymers (all values in wt %)

| VP/VI Copolymer | VI | QVI | VP | LUMA | SMA | PEG for grafting |
|---|---|---|---|---|---|---|
| A [a] | 40 | — | 40 | — | — | 20 [d] |
| B [a] | 60 | — | 40 | — | — | — |
| C [a] | 30 | 30 | 20 | — | — | 20 [e] |
| D [a] | 32 | — | 48 | — | — | 20 [d] |
| E [b] | 40 | — | 50 | — | — | 10 [d] |
| F [b] | 30 | — | 60 | — | — | 10 [d] |
| G [a] | 70 | — | 25 | 5 | — | — |
| H [c] | 30 | — | 40 | — | 10 | 20 [d] |
| I [c] | 40 | — | 40 | 10 | 10 | — |
| J [c] | 78 | — | 20 | — | 2 | — |

[a] including 0.65 wt % PETAE (pentaerythritol allyl ether).
[b] including 0.1 wt % PETAE.
[c] including 0.45 wt % PETAE.
[d] polyethylen glykol, mol mass about 9000 g/mol.
[e] $C_{16-18}$ terminated polyethylene glycol, mol mass about 1400 g/mol.

Example 7

Preparation of Agrochemical Formulation

The compositions 7-1, 7-2 and 7-3 were prepared as follows:

Composition A): Glyphosate isopropylamine salt solution (67.5 wt %, corresponding to about 50 wt % glyphosate free acid), or Roundup® Ultramax (aqueous solution comprising 51 wt % glyphosate isopropylamin salt and 7.5% ethoxylated amine, CAS no. 68478-96-6) was mixed with water and polymer from example 1 and optionally Dispersant A and Dispersant B, and the mixture was intensively mixed for an hour with a dissolver disc.

Composition B): Pyraclostrobin was dissolved in benzylalcohol or in Solvesso® 200 ND.

Both mixtures A) and B) were mixed. The final mixture was intensively mixed at 50° C. for 1 hour with a dissolver disc until a homogeneous emulsion was obtained. The final composition is summarized in Table 4. Samples were taken for storage tests (see Example 8).

TABLE 4

Composition of agrochemical formulations

| Formulation | 7-1 | 7-2 | 7-3 |
|---|---|---|---|
| Glyphosate isopropylamine salt solution | 70% | — | 70% |
| Roundup ® Ultramax | — | 70% | — |
| Polymer from Example 1 | 2% | 2% | 2% |
| Dispersant A | 5% | — | — |
| Dispersant B | 3% | — | — |
| Solvesso ® 200 ND | — | 16% | 16% |
| Benzylalcohol | 16% | — | — |
| Pyraclostrobin | 3.2% | 3.2% | 3.2% |
| Water | up to 100% | up to 100% | up to 100% |

Example 8

Storage stability

The formulations of example 8 were tested as in Example 5 and the results are summarized in Table 5.

TABLE 5

Storage stability

| Polymer No. | Formulation 7-1 | Formulation 7-2 |
|---|---|---|
| A | Stable | n.d. |
| C | Stable | n.d. |
| D | Stable | n.d. |
| E | Stable | Stable |
| F | Stable | Stable |
| H | Stable | Stable |
| I | Stable | Stable |

We claim:

1. A method of producing an aqueous composition, the method comprising:
   adding, as a dispersing agent, a copolymer comprising in about a 1:1 molar ratio
   a) N-vinyllactam, and
   b) vinylimidazole or a quaternized vinylimidazole
   in polymerized form, to water;
   adding a water-insoluble pesticide, the water-insoluble pesticide having a solubility in water of up to 10 g/l at 20° C.; and
   adding at least 35 wt % of a dissolved salt, wherein the salt dissociates in water at 20° C. into at least one anion and at least one cation and wherein the salt contains an anionic pesticide wherein the water-insoluble pesticide comprises pyraclostrobin and wherein the dissolved salt comprises glyphosate.

2. The method according to claim 1, wherein the water-insoluble pesticide is emulsified in the aqueous composition.

3. The method according to claim 1, wherein the copolymer comprises
   a) at least 20 mol % N-vinyllactam, and
   b) at least 1 mol % vinylimidazole or a quaternized vinylimidazole
   in polymerized form.

4. An aqueous composition which contains a copolymer comprising in polymerized form in about a 1:1 molar ratio
   a) N-vinyllactam, and
   b) vinylimidazole or a quaternized vinylimidazole;
   a water-insoluble pesticide, which has a solubility in water of up to 10 g/l at 20° C.; and at least 35 wt % of a dissolved salt, which dissociates in water at 20° C. into at least one anion and at least one cation and which salt contains an anionic pesticide wherein the water-insoluble pesticide comprises pyraclostrobin and wherein the dissolved salt comprises glyphosate.

5. The composition according to claim 4, wherein the water-insoluble pesticide is suspended, and/or emulsified in the aqueous composition.

6. The composition according to claim 4, wherein the copolymer comprises
   a) at least 35 mol % N-vinyllactam, and
   b) at least 5 mol % vinylimidazole or a quaternized vinylimidazole
   in polymerized form.

7. The composition according to claim 4, wherein the composition comprises 1 to 40 wt % of an organic solvent.

8. The composition according to claim 4, wherein the salt contains an organophosphorus herbicide comprising a carboxylic acid group, an aromatic acid herbicide, and/or a phenoxycarboxylic acid herbicide.

9. The composition according to claim 4, wherein the salt contains glufosinate, glufosinate-P, and/or glyphosate.

10. The composition according to claim 7, wherein the organic solvent has a solubility in water of up to 150 g/l at 20° C.

11. A method for preparing the composition as defined in claim 4 by mixing water, the water-insoluble pesticide, the salt and the copolymer.

12. A method for controlling phytopathogenic fungi and/or undesired plant growth and/or undesired attack by insects or mites and/or for regulating the growth of plants, the method comprising applying the composition of claim 4 to a plant or to soil.

* * * * *